US005656149A

United States Patent [19]
Zones et al.

[11] Patent Number: 5,656,149
[45] Date of Patent: Aug. 12, 1997

[54] HYDROCARBON CONVERSION PROCESSES USING ZEOLITE SSZ-41

[75] Inventors: Stacey I. Zones, San Francisco; Donald S. Santilli, Larkspur, both of Calif.

[73] Assignee: Chevron U.S.A. Inc., San Francisco, Calif.

[21] Appl. No.: 646,785

[22] Filed: May 21, 1996

Related U.S. Application Data

[62] Division of Ser. No. 273,068, Jul. 11, 1994, Pat. No. 5,591,421.

[51] Int. Cl.$^6$ .................... C10G 47/02; C10G 35/06; C10G 73/38; C10G 65/02
[52] U.S. Cl. .................... 208/46; 208/108; 208/109; 208/110; 208/113; 208/118; 208/119; 208/120; 208/134; 208/141; 208/27; 208/58; 208/60; 585/407; 585/739; 585/750; 585/467; 585/475; 585/671; 585/666; 585/481; 585/408; 585/733; 585/640
[58] Field of Search .................... 208/46, 108, 109, 208/110, 113, 118, 119, 120, 134, 141, 27, 58, 59, 60; 585/407, 734, 739, 750, 751, 752, 446, 467, 470, 471, 475, 671, 664, 666, 477, 481, 408, 733, 639, 640

[56] References Cited

U.S. PATENT DOCUMENTS

| | | | |
|---|---|---|---|
| 4,670,615 | 6/1987 | Valyocsik | 585/467 |
| 4,670,616 | 6/1987 | DeSimone et al. | 585/467 |
| 4,670,617 | 6/1987 | DeSimone et al. | 502/64 |
| 4,952,744 | 8/1990 | Zones et al. | 585/640 |
| 5,114,565 | 5/1992 | Zones et al. | 208/134 |
| 5,120,425 | 6/1992 | Zones et al. | 208/46 |
| 5,202,014 | 4/1993 | Zones et al. | 208/46 |
| 5,215,648 | 6/1993 | Zones et al. | 208/46 |
| 5,246,566 | 9/1993 | Miller | 208/27 |
| 5,282,958 | 2/1994 | Santilli et al. | 585/739 |
| 5,391,287 | 2/1995 | Nakagawa | 208/46 |
| 5,393,407 | 2/1995 | Zones et al. | 208/46 |
| 5,397,454 | 3/1995 | Zones et al. | 208/46 |
| 5,421,992 | 6/1995 | Zones et al. | 208/46 |
| 5,512,267 | 4/1996 | Davis et al. | 585/407 |

*Primary Examiner*—Glenn A. Caldarola
*Assistant Examiner*—Walter D. Griffin
*Attorney, Agent, or Firm*—R. J. Sheridan

[57] ABSTRACT

The present invention relates to new crystalline zeolite SSZ-41 which comprises oxides of (1) silicon or a mixture of silicon and germanium, and (2) zinc, said zinc being present in an amount from about 2 wt % to about 5 wt % of zinc metal based on the total weight of metals in said zeolite. Zeolite SSZ-41 may also optionally contain oxides of aluminum, iron, gallium or mixtures thereof. Zeolite SSZ-41 has the X-ray diffraction lines of Table I and has an argon adsorption capacity of at least about 0.06 cc/gm at 87° K. Also disclosed are methods of making and using zeolite SSZ-41.

49 Claims, No Drawings

HYDROCARBON CONVERSION PROCESSES USING ZEOLITE SSZ-41

This is a divisional of application Ser. No. 08/273,068, filed Jul. 11, 1994, now U.S. Pat. No. 5,591,421.

BACKGROUND OF THE INVENTION

1. Field of the Invention

The present invention relates to new crystalline zeolite SSZ-41 prepared using a diquaternary ammonium compound comprising a linear polymethylene group having heterocyclic rings bonded to each end of the polymethylene group, each heterocyclic ring containing one or more nitrogen atoms with one nitrogen atom in each ring being quaternary ammonium (hereinafter referred to as the "polymethylene diquat compound, a new method for preparing SSZ-41, and hydrocarbon conversion processes using SSZ-41 as a catalyst.

2. State of the Art

In conventional usage the term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process. The term "zeolite" refers to a molecular sieve containing a silicate lattice, usually in association with some aluminum, boron, gallium, iron, and/or titanium. In the following discussion and throughout this disclosure, the terms molecular sieve and zeolite will be used more or less interchangeably. One skilled in the art will recognize that the teachings relating to zeolites are also applicable to the more general class of materials called molecular sieves.

Natural and synthetic crystalline molecular sieves are useful as catalysts and adsorbents. Each crystalline molecular sieve is distinguished by a crystal structure with an ordered pore structure, and is characterized by a unique X-ray diffraction pattern. Thus, the crystal structure defines cavities and pores which are characteristic of the different species. The adsorptive and catalytic properties of each crystalline molecular sieve are determined in part by the dimensions of its pores and cavities. Accordingly, the utility of a particular molecular sieve in a particular application depends at least partly on its crystal structure.

Because of their unique sieving characteristics, as well as their catalytic properties, crystalline molecular sieves are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

Organic templating agents are believed to play an important role in the process of molecular sieve crystallization. Organic amines and quaternary ammonium cations were first used in the synthesis of zeolites in the early 1960s as reported by R. M. Barrer and P. J. Denny in *J. Chem. Soc.* 1961 at pages 971–982. This approach led to a significant increase in the number of new zeolitic structures discovered as well as an expansion in the boundaries of composition of the resultant crystalline products.

Previously, products with low silica to alumina ratios ($SiO_2/Al_2O_3 \leq 10$) had been obtained, but upon using the organocations as components in the starting gels, zeolites with increasingly high $SiO_2/Al_2O_3$ were realized. Some of these materials are summarized by R. M. Barrer 1982, *Hydrothermal Chemistry of Zeolites*, New York: Academic Press, Inc.

Unfortunately, the relationship between structure of the organocation and the resultant zeolite is far from predictable, as evidenced by the multitude of products which can be obtained using a single quaternary ammonium salt as reported by S. I. Zones et al., 1989, *Zeolites: Facts, Figures, Future*, ed. P. A. Jacobs and R. A. van Santen, pp. 299–309, Amsterdam: Elsevier Science Publishers, or the multitude of organocations which can produce a single zeolitic product as reported by R. M. Barrer, 1989, *Zeolite Synthesis*, ACS Symposium 398, ed. M. L. Occelli and H. E. Robson, pp. 11–27, American Chemical Society.

Thus, it is known that organocations exert influence on the zeolite crystallization process in many unpredictable ways. Aside from acting in a templating role, the organic cation's presence also greatly affects the characteristics of the reaction mixture gel. These effects can range from modifying the gel pH to altering the interactions of the various components via changes in hydration (and thus solubilities of reagents) and other physical properties of the gel. Accordingly, investigators have now begun to consider how the presence of a particular quaternary ammonium salt influences many of these gel characteristics in order to determine more rigorously how such salts exert their templating effects.

In summary, a variety of templates have been used to synthesize a variety of molecular sieves, including zeolites of the silicate, aluminosilicate, and borosilicate families. However, the specific zeolite which may be obtained by using a given template is at present unpredictable. In fact, the likelihood of any given organocation serving as an effective template useful in the preparation of a molecular sieve is conjectural at best. In particular, organocation templating agents have been used to prepare many different combinations of oxides with molecular sieve properties, with silicates, aluminosilicates, aluminophosphates, borosilicates and silicoaluminophosphates being well known examples.

M. J. Annen and M. E. Davis, Microporous Material, Vol. 1, No. 1, February 1993 (pp. 57–65) discloses a zeolite designated VPI-8. From the X-ray pattern provided by Annen and Davis, it appears that VPI-8 has a crystal structure similar to SSZ-41. VPI-8 is described as a high-silica molecular sieve; elemental analysis of ammonium-exchanged VPI-8 giving the following molar composition: 0.009 Zn: 1.00 Si: 0.026 Li. It is further stated that VPI-8 reversibly adsorbs 0.04 g/g argon at 87° K. VPI-8 was prepared from a gel having the following composition: 0.44 $Li_2O$: 0.3 ZnO: $SiO_2$:44 $H_2O$.

A new zeolitic material, designated SSZ-41, has now been discovered. It has a structure similar to VPI-8, but differs from VPI-8 in that SSZ-41 has an argon adsorption capacity greater than (e.g., up to about three times) that reported for VPI-8, and SSZ-41 may contain aluminum (whereas VPI-8 has none).

SUMMARY OF THE INVENTION

In accordance with the present invention, there is provided a zeolite comprising oxides of (1) silicon or a mixture of oxides of silicon and germanium, and (2) zinc, said zinc being present in an amount from about 2 wt % to about 5 wt % of zinc metal based on the total weight of metals in said zeolite, said zeolite having the X-ray diffraction lines of Table I and having an argon adsorption capacity of at least about 0.06 cc/gm at 87° K.

There is also provided in accordance with the present invention a zeolite comprising oxides of (1) silicon or a mixture of silicon and germanium, (2) zinc and (3) aluminum, iron, gallium or mixtures thereof, said zinc being present in an amount from about 2 wt % to about 5 wt % of zinc metal based on the total weight of metals in said zeolite, and said aluminum, iron, gallium or mixtures thereof being present in an amount from about 500 to about 10,000 ppm based on the total weight of metal in the zeolite, said zeolite having the X-ray diffraction lines of Table I.

Also provided in accordance with this invention is a zeolite having a composition, as-synthesized and in the anhydrous state, in terms of mole ratios as follows:

|  | Broad | Preferred |
| --- | --- | --- |
| $YO_2/ZnO$ | 20–100 | 25–50 |
| $YO_2/Q$ | 10–50 | 20–40 | wherein Y comprises silicon or a mixture of silicon and germanium, and Q comprises a polymethylene diquat compound (as defined below), said zeolite having the X-ray diffraction lines of Table I.

In accordance with the present invention there is further provided a zeolite having a composition, as-synthesized and in the anhydrous state, in terms of mole ratios as follows:

|  | Broad | Preferred |
| --- | --- | --- |
| $YO_2/ZnO$ | 20–100 | 25–50 |
| $YO_2/W_2O_3$ | 50–∞ | >70 |
| $YO_2/Q$ | 10–50 | 20–40 | wherein Y comprises silicon or a mixture of silicon and germanium, W comprises aluminum, iron, gallium or mixtures thereof, and Q comprises a polymethylene diquat compound, said zeolite having the X-ray diffraction lines of Table I.

Also provided by this invention are the aforementioned zeolites which, after calcination, have the X-ray diffraction lines of Table II. This invention also provides these calcined zeolites in the hydrogen form, and in the substantially acid-free form.

The present invention also provides a method for preparing a zeolite comprising oxides of (1) silicon or a mixture of silicon and germanium, and (2) zinc, said zinc being present in an amount from about 2 wt % to about 5 wt % of zinc metal based on the total weight of metals in said zeolite, said zeolite having the X-ray diffraction lines of Table I and having an argon adsorption capacity of at least about 0.06 cc/gm at 87° K., said method comprising:

(A) preparing an aqueous mixture comprising (1) sources of an alkali metal or alkaline earth metal oxide, (2) sources of silicon oxide or a mixture of silicon oxide and germanium oxide, (3) sources of zinc oxide, and (4) a polymethylene diquat compound; and (B) maintaining said aqueous mixture under crystallization conditions until crystals of said zeolite form.

This invention also provides a method for preparing a zeolite comprising oxides of (1) silicon or a mixture of silicon and germanium, (2) zinc, said zinc being present in an amount from about 2 wt % to about 5 wt % of zinc metal based on the total weight of metals in said zeolite, and (3) aluminum, iron, gallium or mixtures thereof, said aluminum, iron, gallium or mixtures thereof being present in an amount from about 500 to about 10,000 ppm based on total metal in said zeolite, said zeolite having the X-ray diffraction lines of Table I, said method comprising:

(A) preparing an aqueous mixture comprising (1) sources of an alkali metal or alkaline earth metal oxide, (2) sources of silicon oxide or a mixture of silicon oxide and germanium oxide, (3) sources of zinc oxide, and (4) sources of oxides of aluminum, iron, gallium or mixtures thereof, and (5) a polymethylene diquat compound; and (B) maintaining said aqueous mixture under crystallization conditions until crystals of said zeolite form.

The present invention additionally provides a process for converting hydrocarbons comprising contacting a hydrocarbonaceous feed at hydrocarbon converting conditions with a catalyst comprising the zeolite of this invention.

Further provided by the present invention is a hydrocracking process comprising contacting a hydrocarbon feedstock under hydrocracking conditions with a catalyst comprising the zeolite of this invention.

This invention also includes a dewaxing process comprising contacting a hydrocarbon feedstock under dewaxing conditions with a catalyst comprising the zeolite of this invention.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the zeolite of this invention. Also provided in this invention is such a process wherein the zeolite contains a Group VIII metal component.

Also provided by the present invention is a catalytic cracking process comprising contacting a hydrocarbon feedstock in a reaction zone under catalytic cracking conditions in the absence of added hydrogen with a catalyst comprising the aforementioned hydrogen form of the zeolite of this invention. This invention further includes a catalytic cracking process wherein the catalyst additionally comprises a large pore crystalline cracking component.

The present invention further provides an isomerizing process for isomerizing $C_4$ to $C_7$ hydrocarbons, comprising contacting a catalyst comprising at least one Group VIII metal and the zeolite of this invention in the hydrogen form, with a feed having normal and slightly branched $C_4$ to $C_7$ hydrocarbons under isomerizing conditions. Also provided is such an isomerization process wherein the catalyst has been calcined in a steam/air mixture at an elevated temperature after impregnation of the Group VIII metal, preferably platinum.

This invention also provides a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the zeolite of this invention in the hydrogen form.

This invention additionally provides a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the zeolite of this invention in the hydrogen form.

Further provided by this invention is a process to convert paraffins to aromatics which comprises contacting paraffins with a catalyst comprising the zeolite of this invention in the hydrogen form and, in addition to metals present in said zeolite, gallium, zinc, lead, tin or indium or a compound of gallium, zinc, lead, tin or indium.

This invention also provides a process for converting lower alcohols and other oxygenated hydrocarbons comprising contacting said lower alcohol or other oxygenated hydrocarbon with a catalyst comprising the zeolite of this invention in the hydrogen form under conditions to produce liquid products.

This invention also provides a process for isomerizing olefins comprising contacting said olefin with a catalyst comprising the zeolite of this invention of this invention in its hydrogen form under conditions which cause isomerization of the olefin. One example of such a process is the isomerization of n-butene to isobutene.

The present invention also includes a process for isomerizing polyalkyl substituted aromatics comprising contacting said polyalkyl substituted aromatics under isomerization conditions with a catalyst comprising the zeolite of this invention. The polyalkyl substituted aromatic may comprise a xylene, e.g., m-xylene. The zeolite may be predominantly in the hydrogen form.

In accordance with this invention there is also provided a process for improving the viscosity index of a dewaxed product of waxy hydrocarbon feeds comprising contacting the waxy hydrocarbon feed under isomerization dewaxing conditions with a catalyst comprising a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I. The zeolite may be predominantly in the hydrogen form.

Also included in this invention is a process for producing a $C_{20+}$ lube oil from a $C_{20+}$ olefin feed comprising isomerizing said olefin feed over a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I. The zeolite may be predominantly in the hydrogen form.

Further provided in accordance with the present invention is a process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi with a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixture thereof being present in an amount from about 500 to about 10,000 ppm based on total metal in said zeolite, said zeolite having the X-ray diffraction lines of Table I. The catalyst may be a layered catalyst comprising a first layer comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I, and a second layer comprising an aluminosilicate zeolite which is more shape selective than the zeolite in said first layer. The zeolite may be predominantly in the hydrogen form.

Also included in this invention is a process for preparing a lubricating oil which comprises:

(a) hydrocracking in a hydrocracking zone a hydrocarbonaceous feedstock to obtain an effluent comprising a hydrocracked oil; and (b) catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

The zeolite may be predominantly in the hydrogen form.

Further provided by this invention is a process for isomerization dewaxing a raffinate comprising contacting said raffinate in the presence of added hydrogen with a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I. The raffinate may be bright stock, and the zeolite may be predominantly in the hydrogen form.

The full scope of the present invention will be apparent to those familiar with molecular sieves, their synthesis and use from the following detailed description of the principle features of SSZ-41 and from the examples which accompany the description.

DETAILED DESCRIPTION OF THE INVENTION

Principle Features

The present invention comprises a family of crystalline large pore zeolites, SSZ-41. As used herein the term "large pore" means having an average pore size diameter greater than about 6 Angstroms, preferably greater than about 6.5 Angstroms.

SSZ-41 zeolites can be prepared from an aqueous solution comprising sources of an alkali or alkaline earth metal oxide, a polymethylene diquat compound templating agent, and sources of (1) silicon oxide or a mixture of silicon oxide and germanium oxide, (2) sources of zinc oxide, and, optionally, (3) sources of aluminum oxide, iron oxide, gallium oxide or mixtures thereof. The reaction mixture should have a composition, in terms of mole ratios, within the ranges shown in Tables A and B below.

TABLE A

SSZ-41 REACTION MIXTURE (Si/Zn)

|  | Broad | Preferred |
|---|---|---|
| $YO_2/ZnO$ | 15–75 | 20–40 |
| $OH^-/YO_2$ | 0.10–0.50 | 0.20–0.30 |
| $M^+/YO_2$ | 0.05–0.35 | 0.10–0.20 |
| $H_2O/YO_2$ | 25–60 | 32–44 |
| $Q/Q + M^+$ | 0.33–0.70 | 0.40–0.60 |

TABLE B

SSZ-41 REACTION MIXTURE (Si/Zn/Al)

|  | Broad | Preferred |
|---|---|---|
| $YO_2/W_2O_3$ | 100–2000 | 150–500 |
| $YO_2/ZnO$ | 15–75 | 20–40 |
| $OH^-/YO_2$ | 0.10–0.50 | 0.20–0.30 |
| $M^+/YO_2$ | 0.05–0.35 | 0.10–0.20 |
| $H_2O/YO_2$ | 25–60 | 32–44 |
| $Q/Q + M^+$ | 0.33–0.70 | 0.40–0.60 | wherein Y is silicon or a mixture of silicon and germanium, W is aluminum, iron, gallium or a mixture thereof, Q comprises a polymethylene diquat compound, and M is an alkali metal cation or alkaline earth metal cation.

SSZ-41 has a composition, as-synthesized and in the anhydrous state, in terms of mole ratios indicated in Tables B and C below.

TABLE C

AS-SYNTHESIZED SSZ-41 (Si/Zn)

|  | Broad | Preferred |
|---|---|---|
| $YO_2/ZnO$ | 20–100 | 25–50 |
| $YO_2/M_2O$ | 20–100 | >40 |
| $YO_2/Q$ | 10–50 | 20–40 |

TABLE D

AS-SYNTHESIZED SSZ-41 (Si/Zn/Al)

|  | Broad | Preferred |
|---|---|---|
| $YO_2/W_2O_3$ | ≧50 | ≧70 |
| $YO_2/M_2O$ | 20–100 | >40 |
| $YO_2/Q$ | 10–50 | 20–40 |
| $YO_2/ZnO$ | 20–100 | 25–50 | wherein Y, W, Q and M are as defined above. The as-synthesized SSZ-41 has the X-ray diffraction lines of Table I below.

TABLE I

AS-SYNTHESIZED SSZ-41

| 2Theta | D | Relative Intensity [a] |
|---|---|---|
| 6.71 | 13.16 | S |
| 9.52 | 9.28 | W |
| 20.00 | 4.436 | VS |
| 21.40 | 4.149 | VS |
| 22.19 | 4.003 | S–VS |
| 23.22 | 3.828 | S |
| 24.45 | 3.638 | S–VS |
| 26.07 | 3.415 | M–S |
| 28.01 | 3.183 | M |
| 35.52 | 2.525 | M |

[a] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

The variation in the scattering angle (two theta) measurements, due to instrument error and to differences between individual samples, is estimated at ±0.10 degrees.

The X-ray diffraction pattern of Table I is representative of as-synthesized SSZ-41 zeolites. Minor variations in the diffraction pattern can result from variations in the silica-to-alumina or silica-to-zinc mole ratio of the particular sample due to changes in lattice constants. In addition, sufficiently small crystals will affect the shape and intensity of peaks, leading to significant peak broadening.

After calcination, the SSZ-41 zeolites have a crystalline structure whose X-ray powder diffraction pattern includes the characteristic lines shown in Table II:

TABLE II

CALCINED SSZ-41

| 2Theta | D | Relative Intensity [a] |
|---|---|---|
| 6.82 | 12.95 | VS |
| 9.64 | 9.17 | M–S |
| 20.14 | 4.41 | VS |
| 21.55 | 4.12 | S |
| 22.35 | 3.97 | M |
| 23.38 | 3.80 | M |
| 24.64 | 3.61 | M |
| 26.24 | 3.39 | M |
| 28.18 | 3.16 | M |
| 35.70 | 2.51 | W |

The variation in the scattering angle (two theta) measurements, due to instrument error and to in differences between individual samples, is estimated at ±0.10 degrees.

Representative peaks from the X-ray diffraction pattern of calcined SSZ-41 are shown in Table II. Calcination can also result in changes in the intensities of the peaks as compared to patterns of the "as-synthesized" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

The X-ray powder diffraction patterns were determined by standard techniques. The radiation was the K-alpha/doublet of copper. The peak heights I and the positions, as a function of 2θ where θ is the Bragg angle, were read from the relative intensities, $I/I_o$ where $I_o$ is the intensity of the strongest line or peak, and d, the interplanar spacing in Angstroms corresponding to the recorded lines, can be calculated.

The SSZ-41 zeolites of this invention are also characterized by having an argon adsorption capacity of at least about 0.6 cc/gm at 87° K. Preferably, the argon adsorption capacity of the SSZ-41 zeolites is at least about 0.10 cc/gm at 87° K. This argon adsorption capacity is significantly higher than, e.g., previously mentioned VPI-8.

The argon adsorption capacity of the SSZ-41 zeolites of this invention is measured using an Omnisorp 100CX instrument. Fifty mg samples of SSZ-41 are used. After evacuation of the sample in the cell at room temperature, the temperature is raised to 300° C. while keeping the cell under vacuum. These conditions are held for two hours. The cell and sample are then cooled to 87 Kelvin in a reservoir of liquid argon. In a static micropore filling measurement, doses of argon from a calibrated volume are admitted to the cell at successively higher pressures. The amounts that adsorb from each dose are calculated from the pressure changes. Micropore filling is detected as a step increase in a plot of amount adsorbed versus pressure. The position of the step defines a $P/P_0$ for micropore filling and its size indicates the adsorption capacity of the micropores.

The Preparation of SSZ-41 Zeolites

In preparing SSZ-41 zeolites, a polymethylene diquat compound may be used as a crystallization template in the manner of other well known molecular sieve templating agents. Thus, in general, SSZ-41 is prepared by contacting an active source of (1) silicon oxide or a mixture of silicon oxide and germanium oxide, (2) zinc oxide, and, optionally, (3) aluminum oxide, iron oxide, gallium oxide or mixtures thereof with a polymethylene diquat compound templating agent.

The polymethylene diquat compound templating agents which have been found to produce SSZ-41 comprise compounds comprising a linear polymethylene group having heterocyclic rings bonded to each end of the polymethylene group, each heterocyclic ring containing one or more nitrogen atoms with one nitrogen atom in each ring being quaternary ammonium. These compounds have the general formula:

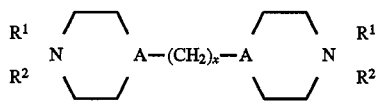

wherein A is carbon or nitrogen, x is 3–10, and $R^1$ and $R^2$ are each lower alkyl when A is carbon, or $R^1$ and $R^2$ form a bicyclic bridge with A when A is nitrogen.

Representative of these compounds are α, ω-di(N-methylpiperidine) polymethylene dicationic compounds and α,ω-di(1,4-diazabicyclo[2,2,21]octane) polymethylene dicationic compounds. These compounds have the following general formulas:

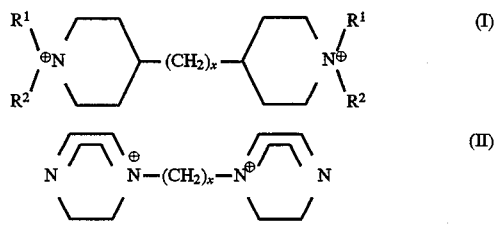

where x is 3–10, and $R^1$ and $R^2$ are at each independent occurrence lower alkyl, e.g., methyl or ethyl, preferably methyl.

Examples of the polymethylene diquat compounds useful in this invention include, but are not limited to, the following:

Typical sources of silicon oxide for the reaction mixture used to make SSZ-41 include silicates, silica hydrogel, silicic acid, fumed silica, colloidal silica, tetra-alkyl orthosilicates, and silica hydroxides. Sources of germanium include tetraalkyl orthogermanates and germanium oxides.

Typical sources of zinc oxide include zinc salts (such as zinc acetate or zinc nitrate). Alternatively, zinc can be ion-exchanged into a Y zeolite, and the resulting product used to make the zeolite of this invention.

Typical sources of aluminum oxide for the reaction mixture include aluminates, alumina and aluminum compounds such as $AlCl_3$, $Al(SO_4)_3$, hydrated $Al(OH)_3$ gels, kaolin clays, colloidal aluminas, and the like. Sources of iron oxide include iron sulfate and iron nitrate, and sources of gallium oxide include gallium sulfate and gallium nitrate.

Alternatively, a zeolite reagent may provide a source of aluminum. In some cases, the source zeolite may provide a source of silica. In that case, the source zeolite in its dealuminated or deboronated form may be used as a source of silica, with additional silicon added using, for example, the conventional sources listed above. Use of a source zeolite reagent as a source of alumina for the present process is described in U.S. Pat. No. 4,503,024 issued on Mar. 5, 1985 to Bourgogne, et al. entitled "PROCESS FOR THE PREPARATION OF SYNTHETIC ZEOLITES, AND ZEOLITES OBTAINED BY SAID PROCESS", the disclosure of which is incorporated herein by reference. Use of a zeolite reagent as a source of alumina constitutes a preferred method of synthesizing aluminum-containing SSZ-41.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, a hydroxide anion for a halide ion in the templating agent, thereby reducing or eliminating the alkali or alkaline earth metal hydroxide quantity required. The alkali metal cation or alkaline earth metal cation may be part of the as-synthesized crystalline oxide material, in order to balance valence electron charges therein.

The reaction mixture is maintained at an elevated temperature until the crystals of the SSZ-41 zeolite are formed. This hydrothermal crystallization is usually conducted under autogenous pressure, at a temperature between 100° C. and 200° C., preferably between 135° and 180° C.

The crystallization period is typically greater than 1 day and preferably from about 3 days to about 7 days. The zeolite can be prepared with or without mild stirring or agitation.

During the hydrothermal crystallization step, the SSZ-41 crystals can be allowed to nucleate spontaneously from the reaction mixture. However, the use of SSZ-41 crystals as seed material can be advantageous in decreasing the time necessary for complete crystallization to occur. In addition, seeding can lead to an increased purity of the product obtained by promoting the nucleation and/or formation of SSZ-41 over any undesired phases. When used as seeds, SSZ-41 crystals are added in an amount between 0.1 and 10% of the weight of silica (or mixture of silicon and germanium oxides) used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized, SSZ-41 zeolite crystals. The drying step can be performed at atmospheric pressure or under vacuum.

Crystalline SSZ-41 can be used as-synthesized or can be thermally treated (calcined). Usually, it is desirable to remove the alkali or alkaline earth metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via ion exchange techniques. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-41. The zeolite can also be impregnated with the metals, or the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249 issued on Jul. 7, 1964 to Plank, et al.; 3,140,251 issued on Jul. 7, 1964 to Plank, et al.; and 3,140,253 issued on Jul. 7, 1964 to Plank, et al., each of which is incorporated by reference herein.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-41, the spatial arrangement of the atoms which form the basic crystal lattice of the zeolite remains essentially unchanged. The exchange of cations has little if any effect on the zeolite lattice structure.

SSZ-41 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the zeolite can be extruded before drying, or, dried or partially dried and then extruded.

SSZ-41 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and copending U.S. Pat. No. 5,316,753, issued May 31, 1994 to Nakagawa, both of which are incorporated by reference herein in their entirety.

Hydrocarbon Conversion Processes

SSZ-41 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-41 are expected to be useful include catalytic cracking, hydrocracking, dewaxing, alkylation, and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., m-xylene), and disproportionating aromatics (e.g., toluene) to provide mixtures of benzene, xylenes and higher methylbenzenes and oxidation reactions. The SSZ-41 catalysts have high selectivity, and under hydrocarbon conversion conditions can provide a high percentage of desired products relative to total products.

SSZ-41 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

SSZ-41 can be used in hydrocarbon conversion reactions with active or inactive supports, with organic or inorganic binders, and with and without added metals. These reactions are well known to the art, as are the reaction conditions.

Hydrocracking

Using SSZ-41 catalyst which contains a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753, issued May 31, 1994 to Nakagawa. Typically, these feedstocks can be hydrocracked at hydrocracking conditions including a temperature in the range of from 175° C. to 485° C., molar ratios of hydrogen to hydrocarbon charge from 1 to 100, a pressure in the range of from 0.5 to 350 bar, and a liquid hourly space velocity (LHSV) in the range of from 0.1 to 30.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation catalyst is present in an effective amount to provide the hydrogenation function of the hydrocracking catalyst, and preferably in the range of from 0.05 to 25% by weight.

Dewaxing

SSZ-41 can be used to dewax hydrocarbonaceous feeds by selectively removing straight chain paraffins. The catalytic dewaxing conditions are dependent in large measure on the feed used and upon the desired pour point.

Generally, the temperature will be between about 200° C. and about 475° C., preferably between about 250° C. and about 450° C. The pressure is typically between about 15 psig and about 3000 psig, preferably between about 200 psig and 3000 psig. The liquid hourly space velocity (LHSV) preferably will be from 0.1 to 20, preferably between about 0.2 and about 10.

Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling about 350° F.

The SSZ-41 hydrodewaxing catalyst may optionally contain a hydrogenation component of the type commonly employed in dewaxing catalysts. See the aforementioned U.S. Pat. No. 4,910,006 and U.S. Pat. No. 5,316,753, issued May 31, 1994 to Nakagawa, for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isodewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

The zeolite of this invention may also be utilized as a dewaxing catalyst in the form of a layered catalyst. That is, the catalyst comprises a first layer comprising zeolite SSZ-41 and at least one Group VIII metal, and a second layer comprising an aluminosilicate zeolite which is more shape selective than zeolite SSZ-41. The use of layered catalysts is disclosed in U.S. Pat. No. 5,149,421, issued Sept. 22, 1992 to Miller, which is incorporated by reference herein in its entirety.

The zeolite of this invention may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig at space velocities (LHSV) between about 0.1 and 20 and a hydrogen recycle rate of about 400 to 1500 SCF/bbl. The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921, 594, issued May 1, 1990 to Miller, which is incorporated by reference herein in its entirety.

The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Aromatics Formation

SSZ-41 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 10 bar, and liquid hourly space velocities (LHSV) ranging from 0.1 to 15.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. No. 4,910,006 and U.S. Pat. No. 5,316,753, issued May 31, 1994 to Nakagawa, for a description of such methods.

The preferred alkali metals are sodium, potassium, and cesium. The zeolite itself can be substantially free of acidity only at very high silica:alumina mole ratios; by "zeolite consisting essentially of silica" is meant a zeolite which is substantially free of acidity without base neutralization.

Catalytic Cracking

Hydrocarbon cracking stocks can be catalytically cracked in the absence of hydrogen using SSZ-41 at liquid hourly space velocities from 0.5 to 50, temperatures from about 260° F. to 1625° F. and pressures from subatmospheric to several hundred atmospheres, typically from about atmospheric to about 5 atmospheres.

For this purpose, the SSZ-41 catalyst can be composited with mixtures of inorganic oxide supports as well as traditional cracking catalyst.

As in the case of hydrocracking catalysts, when SSZ-41 is used as a catalytic cracking catalyst in the absence of hydrogen, the catalyst may be employed in conjunction with traditional cracking catalysts, e.g., any aluminosilicate heretofore employed as a component in cracking catalysts.

Examples of these traditional cracking catalysts are disclosed in the aforementioned U.S. Pat. No. 4,910,006 and U.S. Pat. No. 5,316,753, issued May 31, 1994. When a traditional cracking catalyst (TC) component is employed, the relative weight ratio of the TC to the SSZ-41 is generally between about 1:10 and about 500:1, desirably between about 1:10 and about 200:1, preferably between about 1:2 and about 50:1, and most preferably is between about 1:1 and about 20:1.

The cracking catalysts are typically employed with an inorganic oxide matrix component. See the aforementioned U.S. Pat. No. 4,910,006 and U.S. Pat. No. 5,316,753, issued May 31, 1994 to Nakagawa, for examples of such matrix components.

Oligomerization

It is expected that SSZ-41 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous state phase with SSZ-41 at a temperature of from about 450° F. to about 1200° F., a LHSV of from about 0.2 to about 50 and a hydrocarbon partial pressure of from about 0.1 to about 50 atmospheres.

Also, temperatures below about 450° F. may be used to oligomerize the feedstock, when the feedstock is in the liquid phase when contacting the zeolite catalyst. Thus, when the olefin feedstock contacts the zeolite catalyst in the liquid phase, temperatures of from about 50° F. to about 450° F., and preferably from 80° F. to 400° F. may be used and a WHSV of from about 0.05 to 20 and preferably 0.1 to 10. It will be appreciated that the pressures employed must be sufficient to maintain the system in the liquid phase. As is known in the art, the pressure will be a function of the number of carbon atoms of the feed olefin and the temperature. Suitable pressures include from about 0 psig to about 3000 psig.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the Zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens, et al. which is incorporated totally herein by reference. If required, such zeolites may be obtained by steaming, by use in a conversion process or by any other method which may occur to one skilled in this art.

SSZ-41 can be used to convert light gas $C_2$–$C_6$ paraffins and/or olefins to higher molecular weight hydrocarbons including aromatic compounds. Operating temperatures of 100° C. to 700° C., operating pressures of 0 to 1000 psig and space velocities of 0.5–40 $hr^{-1}$ WHSV (weight hourly space velocity) can be used to convert the $C_2$–$C_6$ paraffin and/or olefins to aromatic compounds. Preferably, the zeolite will contain a catalyst metal or metal oxide wherein said metal is selected from the group consisting of Groups IB, IIB, VIII and IIIA of the Periodic Table, and most preferably gallium or zinc and in the range of from about 0.05 to 5% by weight.

Condensation of Alcohols

SSZ-41 can be used to condense lower aliphatic alcohols having 1 to 10 carbon atoms to a gasoline boiling point hydrocarbon product comprising mixed aliphatic and aromatic hydrocarbon. The condensation reaction proceeds at a temperature of about 500° F. to 1000° F., a pressure of about 0.5 psig to 1000 psig and a space velocity of about 0.5 to 50 WHSV. The process disclosed in U.S. Pat. No. 3,894,107 issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst.

Isomerization

The present catalyst is highly active and highly selective for isomerizing $C_4$ $C_7$ to hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The zeolite may be predominantly in the hydrogen form.

The present process comprises contacting the isomerization catalyst with a hydrocarbon feed under isomerization conditions. The feed is preferably a light straight run fraction, boiling within the range of 30° F. to 250° F. and preferably from 60° F. to 200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

The pressure in the process is preferably between 50 psig and 1000 psig, more preferably between 100 psig and 500 psig. The liquid hourly space velocity (LHSV) is preferably between about 1 to about 10 with a value in the range of about 1 to about 4 being more preferred. It is also preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. The temperature is preferably between about 200° F. and about 1000° F., more preferably between 400° F. and 600° F. See the aforementioned U.S. Pat. No. 4,910,006 and U.S. Pat. No. 5,316,753, issued May 31, 1994 to Nakagawa, for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753, issued May 31, 1994 to Nakagawa, for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753, issued May 31, 1994 to Nakagawa, for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal.

The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-41 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-41.

SSZ-41 can also be used for removing benzene from gasoline by alkylating the benzene as described above and removing the alkylated product from the gasoline.

For high catalytic activity, the SSZ-41 zeolite should be predominantly in its hydrogen ion form. Generally, the zeolite is converted to its hydrogen form by ammonium exchange followed by calcination. If the zeolite is synthesized with a high enough ratio of organo-nitrogen cation to sodium ion, calcination alone may be sufficient. It is preferred that, after calcination, at least 80% of the cation sites are occupied by hydrogen ions and/or rare earth ions.

The pure SSZ-41 zeolite may be used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 weight percent SSZ-41 zeolite. Usually the zeolite content will range from 10 to 90 weight percent, and more typically from 60 to 80 weight percent. The preferred inorganic binder is alumina. The mixture may be formed into tablets or extrudates having the desired shape by methods well known in the art.

Examples of suitable aromatic hydrocarbon feedstocks which may be alkylated or transalkylated by the process of the invention include aromatic compounds such as benzene, toluene, ethylbenzene and xylene. The preferred aromatic hydrocarbon is benzene. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. The preferred olefin is propylene. These olefins may be present in admixture with the corresponding $C_2$ to $C_{20}$ paraffins, but it is preferable to remove any dienes, acetylenes, sulfur compounds or nitrogen compounds which may be present in the olefin feedstock stream, to prevent rapid catalyst deactivation. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F., preferably 250° F. to 450° F. The reaction pressure should be sufficient to maintain at least a partial liquid phase in order to retard catalyst fouling. This is typically 50 psig to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F., but it is preferably about 250° F. to 450° F. The reaction pressure should be sufficient to maintain at least a partial liquid phase, typically in the range of about 50 psig to 1000 psig, preferably 300 psig to 600 psig. The weight hourly space velocity will range from about 0.1 to 10. U.S. Pat. No. 5,082,990 issued on Jan. 21, 1992 to Hsieh, et al. describes such processes and is incorporated herein by reference.

SSZ-41 can also be used in a process for isomerizing polyalkyl substituted aromatics comprising contacting said polyalkyl substituted aromatics under isomerization conditions with a catalyst comprising the zeolite of this invention. The polyalkyl substituted aromatic may comprise a xylene, e.g., m-xylene. The zeolite may be predominantly in the hydrogen form.

SSZ-41 can also be used in a process for improving the viscosity index of a dewaxed product of waxy hydrocarbon feeds comprising contacting the waxy hydrocarbon feed under isomerization dewaxing conditions with a catalyst comprising a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I. The zeolite may be predominantly in the hydrogen form.

SSZ-41 can be used in a process for producing a $C_{20+}$ lube oil from a $C_{20+}$ olefin feed comprising isomerizing said olefin feed over a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I. The zeolite may be predominantly in the hydrogen form.

SSZ-41 can also be used in a process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi with a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I. The catalyst may be a layered catalyst comprising a first layer comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I, and a second layer comprising an aluminosilicate zeolite which is more shape selective than the zeolite in said first layer. The zeolite may be predominantly in the hydrogen form.

SSZ-41 can be used in a process for preparing a lubricating oil which comprises:

(a) hydrocracking in a hydrocracking zone a hydrocarbonaceous feedstock to obtain an effluent comprising a hydrocracked oil; and (b) catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

The zeolite may be predominantly in the hydrogen form.

SSZ-41 can also be used in a process for isomerization dewaxing a raffinate comprising contacting said raffinate in the presence of added hydrogen with a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I. The raffinate may be bright stock, and the zeolite may be predominantly in the hydrogen form. SSZ-41 can also be used as an adsorbent with high selectivities based on molecular sieve behavior and also based upon preferential hydrocarbon packing within the pores.

EXAMPLES

The following examples demonstrate but do not limit the present invention.

Example 1

Preparation of polymethylene diquat compound templating agent

1 Mole of 1,4-diazabicyclo[2.2.2]octane ("DABCO") was dissolved in 500 ml of ethanol and the resulting mixture was cooled in an ice bath. 0.4 Mole of 1,4-diiodobutane was added dropwise to the mixture while stirring. After overnight stirring, the solids which had formed were filtered off and recrystallized by a minimum of warm methanol. The recrystallized product was washed with ether, and then vacuum dried. Microanalytical data was correct for [DABCO-$(CH_2)_4$-DABCO]$^{2+}$2I$^-$ (Template A). Template A has the structure:

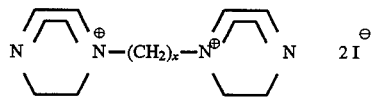

where x=4.

Examples 2–5

Preparation of polymethylene diquat compound templating agents

The procedure of Example 1 was repeated, except that the dibromides indicated below were used instead of the diiodide.

| Ex. No. | Dibromide | Template |
|---|---|---|
| 2 | 1,5-dibromopentane | B |
| 3 | 1,7-dibromoheptane | C |
| 4 | 1,8-dibromooctane | D |
| 5 | 1,9-dibromononane | E |

Templates B-E have the same structure as Template A, except that x in Templates B-E is 5,7,8 and 9, respectively.

Example 6

Preparation of polymethylene diquat compound templating agent

The diquaternary dihalide of bis-4,4-trimethylene-N-methylpiperidine (Template F) was prepared by using the diamine as in Example 1 and slowly adding two equivalents of methyliodide to quaternize both amine sites. Template F has the structure:

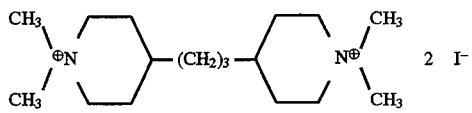

Example 7

Preparation of SSZ-41

A solution was prepared by dissolving 11.01 grams of zinc acetate dihydrate into 450 ml water. 3.00 Grams of Union Carbide Y-52 zeolite ($SiO_2/Al_2O_3=5$) was slurried into the solution. The slurry was allowed to equilibrate at room temperature over several days. The product was collected by filtration and washed several times. Analysis of the dried powder showed about 80% exchange of sodium cations (from the Y-52 zeolite) for zinc cations.

4.41 Grams of a 0.77M solution of Template A was mixed with 2.31 grams of 1N NaOH and 2.64 ml water in a Teflon cup of a 23 ml Parr reactor. 0.28 Gram of the zinc-exchanged Y zeolite and 0.72 gram of Cabosil silica were added and the resulting reaction mixture was heated at 160° C. and 43 RPM for two weeks. The product was analyzed by X-ray diffraction (XRD) which showed a diminished quantity of Y zeolite plus new lines. The product contained several weight percent organic with C/N ratios consistent with Template A.

The reaction was repeated and once again a mixture of phases was produced. The as-made product was slurried in 20 ml of 2N HCl and heated for three days at 85° C. This treatment dissolved away the unreacted zinc-Y zeolite leaving the organo-zeolite phase behind. The XRD pattern was essentially identical to the pattern in Table 1.

Example 8

Preparation of SSZ-41

2 Millimoles of Template A in the hydroxide form was mixed with 2 millimoles of NaOH in 12 ml of water. 0.12 Gram of zinc acetate dihydrate was added and then 0.90 gram of HUA-390 high silica Y zeolite (Tosoh Chemical Corporation, $SiO_2/Al_2O_3$ mole ratio near 300) was added. The reaction mixture was placed in a Parr 4745 reactor and heated for 6 days at 160° C. while being rotated at 45 rpm. The settled crystalline product was collected by filtration, washed and dried. The product had the X-ray diffraction pattern of SSZ-41 as shown in Table I.

Example 9

Preparation of SSZ-41

81 Grams of a 0.74M solution of Template A was mixed with 66 grams of 1N NaOH and 210 ml of water in the Teflon liner for a Parr 600 ml autoclave. 3.0 Grams of zinc acetate dihydrate, 27 grams of HUA-390 high silica Y zeolite and 0.50 gram of SSZ-41 (uncalcined seed material) were added. The reaction mixture was heated to 160° C. over a thirty-hour period and then held at 160° C. for five days while being stirred at 100 rpm. The resulting product was SSZ-41.

Example 10

Calcined SSZ-41

Dried, as-synthesized SSZ-41 was calcined in air to 600° C. with the ramp-up proceeding in 60° C./hr steps. The product lost about 10% mass. The X-ray diffraction of the product was consistent with the pattern given in Table II above. The product was given one ion-exchange using an equal mass of ammonium nitrate to zeolite and a dilution of 20 cc/gm zeolite. The solution was heated for a minimum of two hours at 95° C. The zeolite was then filtered and washed. A dried sample gave a micropore volume (nitrogen) of 0.11 cc and a surface area of about $300M^2/gm$. Not much zinc was removed during the ion exchange, the zinc typically comprising about 3–5 wt % of the product. The $SiO_2/Al_3O_3$ mole ratio was about 200.

Examples 11–14

Preparation of SSZ-41

In the following examples, the procedure of Example 8 was repeated using the templating agents indicated below.

| Ex. No. | Template | Product |
|---|---|---|
| 11 | B | SSZ-41 |
| 12 | C | SSZ-41 + trace of ZSM-12 |
| 13 | D | SSZ-41 + trace of ZSM-12 |
| 14 | E | Amorphous + SSZ-41 |

Example 15

171 Grams of a 0.62M solution of Template A was mixed with 106 grams of 1N NaOH, 4.82 grams of zinc acetate dihydrate and 189 grams of water in the Teflon liner of a Parr 1 liter reactor. 44 Grams of HUA-39 high silica Y zeolite was added along with 1 Gram of SSZ-41 seed material. The reactants were heated up to 160° C. using a 30-hour ramp-up program. The reaction mixture was held at this temperature while being stirred at 100 rpm. The product was recovered by filtration and, after washing and drying, was found to show the X-ray diffraction pattern given in Table III below.

TABLE III

| 2Theta | D | 100 I/I$_o$ |
|---|---|---|
| 6.762 | 13.0614 | 52.3 |
| 9.552 | 9.2517 | 15.4 |

TABLE III-continued

| 2Theta | D | 100 I/I$_o$ |
|---|---|---|
| 13.475 | 6.5658 | 4.4 |
| 13.721 | 6.4486 | 4.1 |
| 16.078 | 5.5082 | 3.1 |
| 18.864 | 4.7005 | 3.5 |
| 20.071 | 4.4204 | 100.0 |
| 21.478 | 4.1339 | 95.1 |
| 22.270 | 3.9887 | 56.3 |
| 23.290 | 3.8162 | 47.1 |
| 24.527 | 3.6265 | 56.5 |
| 26.159 | 3.4038 | 35.2 |
| 28.079 | 3.1753 | 45.4 |
| 29.721 | 3.0035 | 3.1 |
| 32.610 | 2.7437 | 9.7 |
| 35.607 | 2.5193 | 19.6 |
| 36.958 | 2.4303 | 5.4 |
| 38.691 | 2.3253 | 3.9 |
| 39.371 | 2.2867 | 4.3 |

Example 16

Calcination of SSZ-41

A sample of the product from Example 15 was subjected to calcination as follows. The sample was heated in a muffle furnace from room temperature to 600° C. in stages and in air. The stages were to 125° C. at 50° C./hr, hold for two hours, 50° C./hr to 540° C., hold for four hours, 50° C./hr to 600° C. with a final hold for four hours.

Example 17

Ion Exchange of SSZ-41

The product of Example 16 was ion exchanged using a 1/1/50 ratio for zeolite/ammonium nitrate/water. The solution was heated to 95° C. for two hours and then cooled. The solids were filtered off and washed.

Example 18

Constraint Index determination

The product of Example 17 was pelleted at 3000 psi, broken and sieved to 20-40 mesh size. 0.50 Gram of the zeolite was loaded into a stainless steel tube reactor with alundum on both sides of the zeolite bed. The reactor was placed in a Lindburg furnace and heated to 540° C. for drying. At 125° C. helium was introduced into the reactor at 10 cc/minute and atmospheric pressure. Feed was introduced by means of a syringe pump at a rate of 0.62 cc/hr of a 50/50 (v/v) mixture of n-hexane and 3-methylpentane. The reaction was run at about 426° C. The conversion after ten minutes was 26% and the C.I. was 0.50, indicating that the pores in SSZ-41 are probably at least 12 ring.

Example 19

Conversion of methanol to aromatics

The catalyst from Example 18 was used to evaluate the ability of SSZ-41 to convert methanol into higher hydrocarbons. The experiment was run as described in Example 18, using a down flow reactor, syringe pump and on-line GC, but in this experiment the feed was methanol delivered at about 399° C. The product distribution, via area count from the GC as the catalyst was operating at five minutes on stream and 100% conversion, is indicated below.

| Hydrocarbon | Area % |
|---|---|
| Methane | 1.36 |
| Ethane/Ethylene | 2.21 |
| Propane/Propylene | 19.04 |
| Isobutane | 8.00 |
| Pentanes | 4.42 |
| Hexanes | 1.36 |
| Benzene | 0.50 |
| Toluene | 1.70 |
| Xylenes | 6.30 |
| Aromatic C$_9$ | 18.00 |
| Aromatic C$_{10}$ | 24.65 |
| Aromatic C$_{11}$ | 12.10 |
| Hexamethylbenzene | 0.50 |

The product distribution can be seen to be skewed toward a heavier aromatic distribution than is typically seen with a 10-ring ZSM-5 catalyst.

Example 20

Preparation of palladium SSZ-41

1 Gram of ammonium-exchanged SSZ-41 from Example 17 was slurried into a mixture of 9 ml water and 1 ml of 0.15N ammonium hydroxide solution. Enough palladium tetramine dinitrate, buffered in ammonium hydroxide, was added to give 0.5 wt % palladium on the zeolite at complete ion exchange. The exchange was carried out at room temperature for three days, after which the catalyst was filtered, washed and dried. The resulting material was calcined to 482° C. (900° F.), the temperature being raised in stages and held at the final temperature of 482° C. for three hours. The calcined catalyst was then pelleted, crushed and sieved as described in Example 18.

Example 21

Hydrocracking with Pd SSZ-41

The catalyst from Example 20 was loaded into a stainless steel reactor and heated to 538° C. (1000° F.) in nitrogen for drying. The temperature was reduced to 121° C. (250° F.) and then slowly raised in hydrogen at 1200 psi. A feed of n-hexadecane was begun and data was taken at 332° C. (630° F.) with the feed at 1.55 whsv. At 21.8 hours at this temperature, the hexadecane conversion was 95.6% with a very good isomerization selectivity of 79.3%. In addition, the iso/n ratio for most of the hydrocracked products was between 1 and 2, indicating considerable product shape-selectivity.

Example 22

Preparation of SSZ-41

The procedure of Example 8 was repeated except that Template F was used. The product was recovered after 11 days and was found by XRD to be a mixture of SSZ-41 and some ZSM-12.

Example 23

Preparation of platinum SSZ-41

The procedure of Example 20 was repeated, except that platinum was used (in the same weight percent) rather than palladium. The resulting Pt SSZ-41 was calcined to only 288° C. (550° F.) for three hours and in air. 15 Grams of zeolite SSZ-41 was platinum exchanged.

Example 24

Hydrodewaxing with Pt SSZ-41

The catalyst prepared in Example 23 was pelleted, crushed and sieved to 24–40 mesh size. The catalyst (15 cc) was loaded into a stainless steel reactor and a feed was hydrodewaxed. The feed properties are given in Table E below. The run conditions and product data are provided in Table F below.

TABLE E

Properties of Hydrocracked Feedstock For Upgrade by Paraffin Dewaxing (Hydrodewaxing)

|  | MN[1] | LN[2] | SW[3] | HN[4] |
|---|---|---|---|---|
| API Gravity | 31.3 | 30.8 | 32.1 | 29.6 |
| Nitrogen (ppm) | 3.71 | 3.96 | 0.62 | 4.36 |
| Sulfur (ppm) | 2.89 | 10 | 6 | 10 |
| Waxes (wt %) | 10.4 | 7.9 | 93.3 | 18 |
| V.I. | 120 | 96 | — | — |
| Pour point (°C.) | 35 | 24 | 81 | 54 |
| Visc. (cst @ 40° C.) | 33.7 | 19.92 | — | — |
| Avg. mol. wt. | 407 | 356 | 620 | 534 |

[1]Medium neutral
[2]Light neutral
[3]Slack wax
[4]Heavy neutral

TABLE F

Run Data For Dewaxing with Pt SSZ-41

| WHSV-1 | 1.26 | 2.16 | 0.52 | 2.15 |
|---|---|---|---|---|
| Gas rate, SCF H$_2$/bbl | 4820 | 5000 | 6600 | 5060 |
| psig | 2300 | 2300 | 2300 | 2300 |
| Constant pour point (°C.) | −13 | −13 | −9 | −13 |
| Titrated? | Yes | Yes | Yes | Yes |
| Temp. (°C./°F.) | 338/640 | 346/655 | 338/640 | 354/670 |
| Yield, 370° C.+ (%) | 86 | 84 | 58 | 81 |
| Gas yield (%) | 0.4 | 0.2 | 2 | 1 |
| V.I. | 106 | 86 | 129 | 95 |
| Visc. (cst @ 40° C.) | 35.4 | 20.1 | 52.0 | 102.9 |
| Visc. (cst @ 100° C.) | 5.8 | 4.0 | 8.2 | 11.3 |
| Cloud point (°C.) | −8 | −9 | −7 | −16 |

Example 25

Preparation of platinum SSZ-41 and use as a dehydrogenation catalyst

Aluminum-free SSZ-41 was prepared as in Example 15. Subsequent steps to calcine, ammonium ion-exchange, platinum exchange and recalcine at 288° C. (550° F.) were carried out as described in Examples 16, 17 and 23, respectively. The resulting Pt-SSZ-41 was then pelleted, broken up, sieved and loaded into a reactor in order to run a Constraint index reaction as described in Example 18. The reaction was carried out at 427° C. (800° F.) as with a normal cracking reaction. No supplemental hydrogen was supplied. The data shown below in Table G demonstrate that the aluminum-free SSZ-41 can be used to prepare an active dehydrogenation catalyst.

TABLE G

| Reaction Conditions | |
|---|---|
| Temp. (°C./°F.) | 427/800 |
| WHSV (−1) | 0.82 |
| Pressure | Atmospheric |
| Helium/Feed ratio | 6 |
| Feed - n-Hexane/3-methyl Pentane ratio | 1/1 |
| Time on stream | 100 min. |

| Results | |
|---|---|
| Conversion | 41% |
| Isomerization selectivity | 10% |
| C$_5$_ cracking selectivity | 5% |
| Aromatization selectivity | 12% |
| Dehydrogenation selectivity | 56% |
| Other | 17% |

Example 26

Argon adsorption capacity of SSZ-41

A sample of the calcined Si/Zn SSZ-41 material from Example 16 was tested for its argon adsorption capacity by the method described above and was found to have a micropore volume of 0.094 cc/gm. (The value for nitrogen is 0.10 cc/gm for this same sample.) A calcined Si/Zn/Al SSZ-41 sample had a comparable argon value, 0.098 cc/gm.

What is claimed is:

1. A process for converting hydrocarbons comprising contacting a hydrocarbonaceous feed at hydrocarbon converting conditions with a catalyst comprising a zeolite comprising oxides of (1) silicon or a mixture of silicon and germanium, and (2) zinc, said zinc being present in an amount from about 2wt % to about 5 wt % of zinc metal based on the total weight of metals in said zeolite, said zeolite having the X-ray diffraction lines of Table I and having an argon adsorption capacity of at least about 0.06 cc/gm at 870 K.

2. The process of claim 1 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with the catalyst.

3. The process of claim 2 wherein the zeolite is substantially free of acidity.

4. The process of claim 2 wherein the zeolite contains a Group VIII metal component.

5. The process of claim 1 wherein the process is a process to convert paraffins to aromatics which comprises contacting paraffins with the catalyst, said catalyst comprising, in addition to metals in the zeolite, gallium, zinc, or a compound of gallium or zinc.

6. A process for converting hydrocarbons comprising contacting a hydrocarbonaceous feed at hydrocarbon converting conditions with a catalyst comprising a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

7. The process of claim 6 wherein the process is a hydrocracking process comprising contacting a hydrocarbon feedstock under hydrocracking conditions with the catalyst.

8. The process of claim 7 wherein the zeolite is predominantly in the hydrogen form.

9. The process of claim 6 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with the catalyst.

10. The process of claim 9 wherein the zeolite is substantially free of acidity.

11. The process of claim 9 wherein the zeolite contains a Group VIII metal component.

12. The process of claim 6 wherein the process is a catalytic cracking process comprising contacting a hydrocarbon feedstock in a reaction zone under catalytic cracking conditions in the absence of added hydrogen with the catalyst.

13. The process of claim 12 wherein the zeolite is predominantly in the hydrogen form.

14. The process of claim 6 wherein the process is an isomerizing-process for isomerizing $C_4$ to $C_7$ hydrocarbons, comprising contacting the catalyst with a feed having normal and slightly branched $C_4$ to $C_7$ hydrocarbons under isomerizing conditions, said catalyst being impregnated with at least one Group VIII metal.

15. The process of claim 14 wherein the zeolite is predominantly in the hydrogen form.

16. The process of claim 14 wherein the catalyst has been calcined in a steam/air mixture after impregnation of the Group VIII metal.

17. The process of claim 14 wherein the Group VIII metal is platinum.

18. The process of claim 6 wherein the process is a process for alkylating an aromatic hydrocarbon which comprises contacting under alkylation conditions at least a mole excess of an aromatic hydrocarbon with a $C_2$ to $C_{20}$ olefin under at least partial liquid phase conditions and in the presence of the catalyst.

19. The process of claim 18 wherein the olefin is a $C_2$ to $C_4$ olefin.

20. The process of claim 18 wherein the aromatic hydrocarbon is selected from the group consisting of benzene, toluene, xylene, or mixtures thereof.

21. The process of claim 18 wherein the zeolite is predominantly in the hydrogen form.

22. The process of claim 6 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

23. The process of claim 22 wherein the aromatic hydrocarbon is a member selected from the group consisting of benzene, ethylbenzene, toluene, xylene, or mixtures thereof.

24. The process of claim 22 wherein the polyalkyl aromatic hydrocarbon is a dialkylbenzene.

25. The process of claim 22 wherein the zeolite is predominantly in the hydrogen form.

26. The process of claim 6 wherein the process is a process to convert paraffins to aromatics which comprises contacting paraffins with the catalyst, said catalyst comprising, in addition to metals in the zeolite, gallium, zinc, or a compound of gallium or zinc.

27. The process of claim 26 wherein the zeolite is predominantly in the hydrogen form.

28. The process of claim 6 wherein the process is a process for isomerizing olefins comprising contacting said olefin under conditions which cause isomerization of the olefin with the catalyst.

29. The process of claim 28 wherein the zeolite is predominantly in the hydrogen form.

30. The process of claim 6 wherein the process is a process for isomerizing polyalkyl substituted aromatics comprising contacting said polyalkyl substituted aromatics under isomerization conditions with the catalyst.

31. The process of claim 30 wherein the polyalkyl substituted aromatic comprises a xylene.

32. The process of claim 31 wherein the xylene is m-xylene.

33. The process of claim 30 wherein the zeolite is predominantly in the hydrogen form.

34. A dewaxing process comprising contacting a hydrocarbon feedstock under dewaxing conditions with a catalyst comprising a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

35. The process of claim 34 wherein the zeolite is predominantly in the hydrogen form.

36. A process for improving the viscosity index of a dewaxed product of waxy hydrocarbon feeds comprising contacting the waxy hydrocarbon feed under isomerization dewaxing conditions with a catalyst comprising a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metal in said zeolite and said aluminum, iron, gallium or mixtures thereof being present in an amount from about 500 to about 10,000 ppm based on total metal in said zeolite, said zeolite having the X-ray diffraction lines of Table I.

37. The process of claim 36 wherein the zeolite is predominantly in the hydrogen form.

38. A process for producing a $C_{20+}$ lube oil from a $C_{20+}$ olefin feed comprising isomerizing said olefin feed over a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

39. The process of claim 38 wherein the zeolite is predominantly in the hydrogen form.

40. A process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi with a catalyst comprising at least one Group VIII metal and a zeolite comprising oxides of (1)

silicon or a mixture of silicon and germanium, (2) zinc, and (3) aluminum, iron, gallium or mixtures thereof, said zinc being present in an amount from about 2 wt % to about wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

41. A process according to claim 40 wherein said catalyst comprises a layered catalyst comprising a first layer comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I, and a second layer comprising an aluminosilicate zeolite which is more shape selective than the zeolite in said first layer.

42. The process of claim 40 wherein the zeolite is predominantly in the hydrogen form.

43. A process for preparing a lubricating oil which comprises:

(a) hydrocracking in a hydrocracking zone a hydrocarbonaceous feedstock to obtain an effluent comprising a hydrocracked oil; and (b) catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

44. The process of claim 43 wherein the zeolite is predominantly in the hydrogen form.

45. A process for isomerization dewaxing a raffinate comprising contacting said raffinate in the presence of added hydrogen with a catalyst comprising at least one Group VIII metal and a zeolite comprising oxides of (1) silicon or a mixture of silicon and germanium, (2) zinc, and (3) aluminum, iron, gallium or mixtures thereof; said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

46. The process of claim 45 wherein the raffinate is bright stock.

47. The process of claim 45 wherein the zeolite is predominantly in the hydrogen form.

48. A process for converting lower alcohols and other oxygenated hydrocarbons comprising contacting said lower alcohol or other oxygenated hydrocarbon under conditions to produce liquid products with a catalyst comprising a zeolite comprising oxides of (1) silicon or a mixture of silicon and germanium, (2) zinc, and (3) aluminum, iron, gallium or mixtures thereof, said zinc being present in an amount from about 2 wt % to about 5 wt % of zinc metal based on the total weight of metals in said zeolite and said aluminum, iron, gallium or mixtures thereof being present in an amount from about 500 to about 10,000 ppm based on total metal in said zeolite, said zeolite having the X-ray diffraction lines of Table I.

49. The process of claim 48 wherein the zeolite is predominantly in the hydrogen form.

\* \* \* \* \*